United States Patent
Harris et al.

(10) Patent No.: US 12,366,242 B2
(45) Date of Patent: Jul. 22, 2025

(54) HYDRAULIC FRACTURING PUMP HEALTH AND PERFORMANCE MONITORING USING IoT SENSOR NETWORKS

(71) Applicant: SPM Oil & Gas Inc., Fort Worth, TX (US)

(72) Inventors: Ralph E. Harris, Fort Worth, TX (US); Trevor Davis, Mansfield, TX (US); Brian Cheng, Trophy Club, TX (US); Taylor Fry, Dallas, TX (US)

(73) Assignee: SPM Oil & Gas Inc., Fort Worth, TX (US)

( * ) Notice: Subject to any disclaimer, the term of this patent is extended or adjusted under 35 U.S.C. 154(b) by 386 days.

(21) Appl. No.: 17/905,589

(22) PCT Filed: Mar. 3, 2021

(86) PCT No.: PCT/US2021/020761
§ 371 (c)(1),
(2) Date: Sep. 2, 2022

(87) PCT Pub. No.: WO2021/178602
PCT Pub. Date: Sep. 10, 2021

(65) Prior Publication Data
US 2023/0044928 A1 Feb. 9, 2023

Related U.S. Application Data

(60) Provisional application No. 62/984,766, filed on Mar. 3, 2020.

(51) Int. Cl.
*F04B 51/00* (2006.01)
*E21B 43/26* (2006.01)
(Continued)

(52) U.S. Cl.
CPC .......... *F04B 51/00* (2013.01); *E21B 43/2607* (2020.05); *F04B 15/02* (2013.01);
(Continued)

(58) Field of Classification Search
CPC ........ F04B 51/00; F04B 15/02; F04B 49/065; F04B 2201/0402; F04B 2201/0404;
(Continued)

(56) References Cited

U.S. PATENT DOCUMENTS 11,015,536 B2 * 5/2021 Yeung ...................... F02C 9/40
11,149,533 B1 * 10/2021 Yeung .................... F04B 15/02
(Continued)

FOREIGN PATENT DOCUMENTS

WO 2016090566 A1 6/2016

OTHER PUBLICATIONS

Translation of WO2016090566.*
International Search Report and Written Opinion issued in Application No. PCT/US2021/20761; Dated May 24, 2021, 19 Pages.

*Primary Examiner* — Helen C Kwok (57) ABSTRACT

A system for monitoring a piece of hydraulic fracturing equipment such as a positive displacement pump. The system includes a plurality of sensors configured to detect conditions of the hydraulic fracturing pump and a processor that is communicatively coupled to the plurality of sensors and configured to analyze data received from the plurality of sensors. The processor is also configured to predict faults in the hydraulic fracturing pump based on the data analysis. The system also includes a communication interface that is configured for transmitting predicted fault data to one or more devices.

26 Claims, 10 Drawing Sheets

(51) Int. Cl.
  *F04B 15/02*  (2006.01)
  *F04B 49/06*  (2006.01)
  *H04L 67/12*  (2022.01)
(52) U.S. Cl.
  CPC ............ *F04B 49/065* (2013.01); *H04L 67/12* (2013.01); *F04B 2201/0402* (2013.01); *F04B 2201/0404* (2013.01); *F04B 2201/0802* (2013.01); *F04B 2201/1201* (2013.01); *F04B 2201/1208* (2013.01); *F04B 2205/02* (2013.01); *F04B 2205/04* (2013.01)
(58) Field of Classification Search
  CPC ...... F04B 2201/0802; F04B 2201/1201; F04B 2201/1208; F04B 2205/02; F04B 2205/04; E21B 43/2607; H04L 67/12
  See application file for complete search history.

(56)  References Cited

U.S. PATENT DOCUMENTS

| | | | |
|---|---|---|---|
| 2010/0037639 A1* | 2/2010 | Ogden | F25B 9/00 |
| | | | 62/127 |
| 2016/0107768 A1* | 4/2016 | Nicks | B64F 5/60 |
| | | | 702/183 |
| 2016/0195082 A1* | 7/2016 | Wiegman | F04B 23/04 |
| | | | 417/63 |
| 2017/0218843 A1* | 8/2017 | Oehring | H02K 7/1823 |
| 2019/0356740 A1* | 11/2019 | Yuan | H04Q 9/00 |

* cited by examiner

FIG. 11

HYDRAULIC FRACTURING PUMP HEALTH AND PERFORMANCE MONITORING USING IoT SENSOR NETWORKS

CROSS-REFERENCE TO RELATED APPLICATIONS

This Patent Application is a 371 national stage of PCT Application No. PCT/US2021/020761, filed on Mar. 3, 2021, entitled "HYDRAULIC FRACTURING PUMP HEALTH AND PERFORMANCE MONITORING USING IOT SENSOR NETWORKS," which claims priority to U.S. Provisional Application No. 62/984,766, filed on Mar. 3, 2020, entitled "HYDRAULIC FRACTURING PUMP HEALTH AND PERFORMANCE MONITORING USING IOT SENSOR NETWORKS," and assigned to the assignee hereof. The disclosures of the prior Applications are considered part of and are incorporated by reference into this Patent Application.

FIELD

The present disclosure relates to IoT sensor networks, and in particular, to a system and method for hydraulic fracturing pump health and performance monitoring using IoT sensors.

BACKGROUND

Hydraulic fracturing is a process to obtain hydrocarbons such as natural gas and petroleum by injecting a fracking fluid or slurry at high pressure into a wellbore to create cracks in deep rock formations. The hydraulic fracturing process employs a variety of different types of equipment at the site of the well, including one or more positive displacement pumps, slurry blender, fracturing fluid tanks, high-pressure flow iron (pipe or conduit), wellhead, valves, charge pumps, and trailers upon which some equipment are carried.

Positive displacement or reciprocating pumps are commonly used in oil fields for high pressure hydrocarbon recovery applications, such as injecting the fracking fluid down the wellbore. A positive displacement pump may include one or more plungers driven by a crankshaft to create a high or low pressure in a fluid chamber. A positive displacement pump typically has two sections, a power end and a fluid end. The power end includes a crankshaft powered by an engine that drives the plungers. The fluid end of the pump includes cylinders into which the plungers operate to draw fluid into the fluid chamber and then forcibly push out at a high pressure to a discharge manifold, which is in fluid communication with a well head.

DETAILED DESCRIPTION

The system and method for hydraulic fracturing pump health and performance monitoring can be used on hydraulic fracturing pumps during operation in a hydraulic fracturing operation. For example, the system and method can be used on a crankshaft driven high pressure piston diaphragm pump designed to handle abrasive mineral ores, tailings slurries and mine water, which cause wear on components of the pump. The system can be applied to OEM pumps and can also be retrofitted onto any existing pump. The system and method may also be used, in alternative implementations, on a number of different pieces of equipment commonly found at a hydraulic fracturing site, such as positive displacement pumps, slurry blender, charge pump (which is typically a centrifugal pump), and other equipment. Monitoring the operation of such equipment can allow timely inspection, maintenance, and replacement to be scheduled to ensure optimal operations and/or reduce disruptions. Conventionally, data from sensors are collected and transmitted to a remote central processing unit where they are analyzed and optionally reported to customers, operators, etc. The system and method for hydraulic fracturing pump health and performance monitoring described in this specification instead uses edge computing (i.e., at or near the source of the data) and smart sensors to provide actionable messages to users locally and in real time.

The use of the system and method described herein can help prevent unplanned or unscheduled downtime, prevent premature failure of components of hydraulic fracturing pumps, increase understanding of the "true" age of the machine from an operational perspective, and drive better maintenance practices for hydraulic fracturing operations. The system uses mixed mode electronics for signal processing, which have low power requirements, are low cost, and allow "throw away" sensors (i.e., inexpensive and/or easily replaceable sensors) that provide real time fault detection at or near the hydraulic fracturing site and that identify precursors to emerging faults. In exemplary embodiments, the system includes one or more of the following types of sensors: position sensor, proximity sensor, inductive sensor, temperature sensor, pressure sensor, vibration sensor, and accelerometer. As further examples, the system includes one or more lubrication input oil quality sensor 92, a lubrication input temperature sensor 94, a lubrication input pressure sensor 96, and a crankshaft position sensor 98. More specifically, the group of sensors used herein include: a crankshaft rotation sensor that is operably coupled to the power end; a power end triaxial accelerometer that is mounted on, or otherwise operably coupled to, the power end; lubrication supply pressure sensors that are operably coupled to the high pressure lubrication line and the low pressure lubrication line; lubrication supply temperature sensors that are operably coupled to the high pressure lubrication line and the low pressure lubrication line; cylinder drain pan temperature sensors that are operably coupled to cylinder drain pans of the power end; a fluid end triaxial accelerometer that is mounted on, or otherwise operably coupled to, the fluid end; a suction slurry pressure sensor that is operably coupled to the fluid end; a suction slurry temperature sensor that is operably coupled to the fluid end; and a discharge slurry pressure sensor that is operably coupled to the fluid end.

Figure 1:
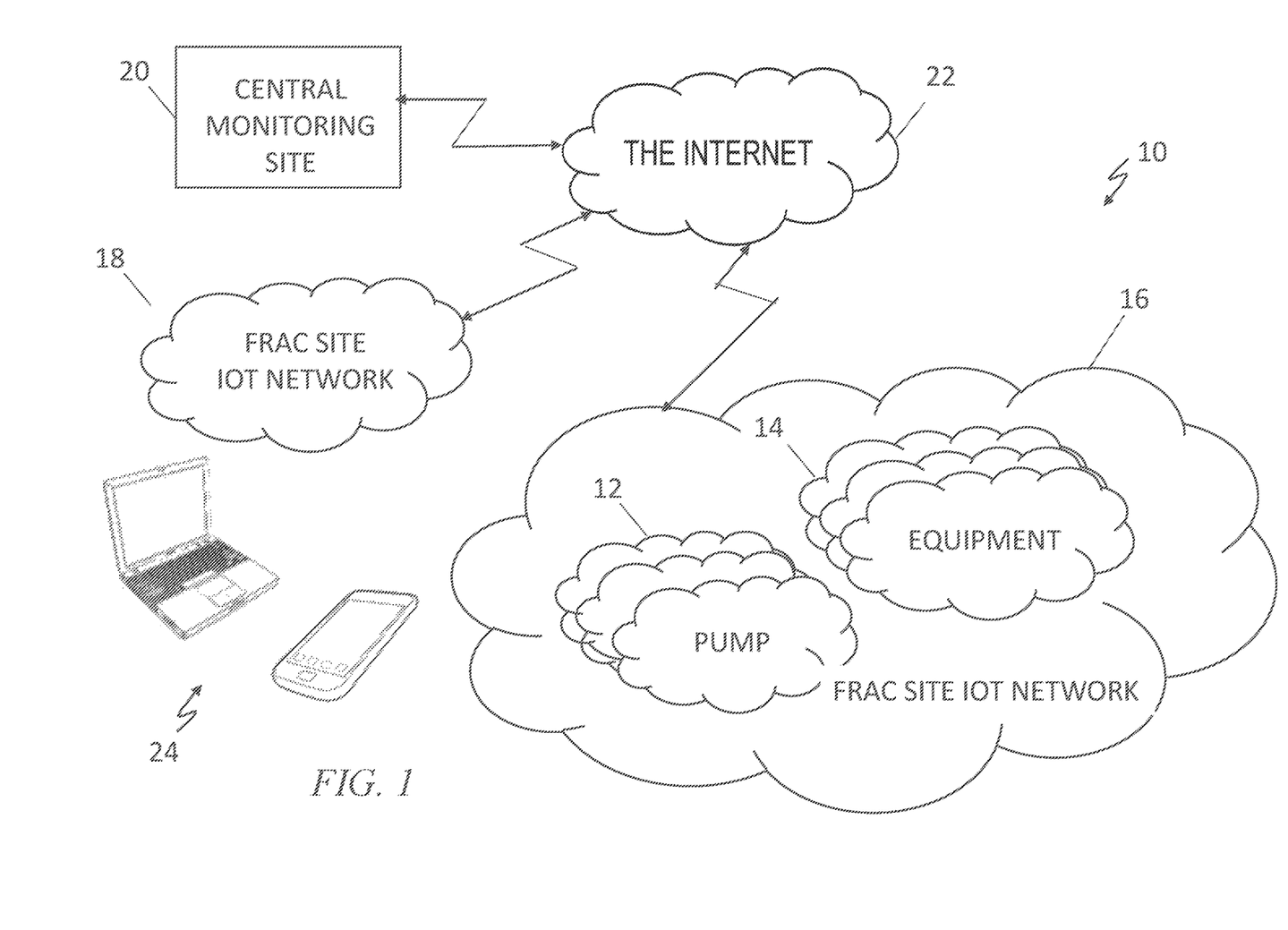
FIG. 1 is a simplified block diagram of a system and method for monitoring frac site equipment using IoT sensors according to the teachings of the present disclosure.

In an exemplary embodiment, a system and method 10 for monitoring hydraulic fracturing pumps and other equipment at one or more frac sites is shown in FIG. 1. Systems 10 may include a plurality of IoT networks (also known as fog networks) 12 and 14 formed of a plurality of sensors, smart sensors, and other devices that communicate with one another at one or more frac sites 16 and 18. The IoT network(s) at each frac site are further in communication with a central monitoring site 20 via the Internet 22 (which may include computer networks, local area networks, wide area networks, cellular networks, and satellite networks). The network nodes of the IoT network may communicate via one or more wireless protocols, such as WiFi, WiFi Direct (device-to-device or D2D), Bluetooth, ZigBee, ZWave, CANBUS/J1939, cellular, or other wireless technologies now known or to be developed. The network nodes are comprised of sensors that measure a variety of operating parameters of equipment used in oil and gas exploration and production operations. Further, one or more types of user interface devices 24 such as mobile phones, tablet computers, laptop computers, and the like may be used to communicate with one or more of the nodes in the IoT networks.

At the heart of each frac site are equipment including positive displacement pumps, slurry blenders, charge pumps (which is typically a centrifugal pump), water trucks, sand trucks, chemicals, manifold assemblies, and trailers. Each hydraulic fracturing pump receives fracturing slurry or fluid at a relatively low pressure and discharges the fracturing slurry or fluid at a high pressure (up to 15,000-30,000 psi) that is transmitted to a manifold assembly to a wellhead inside a wellbore extending down to subterranean geoformations.

Figure 2:
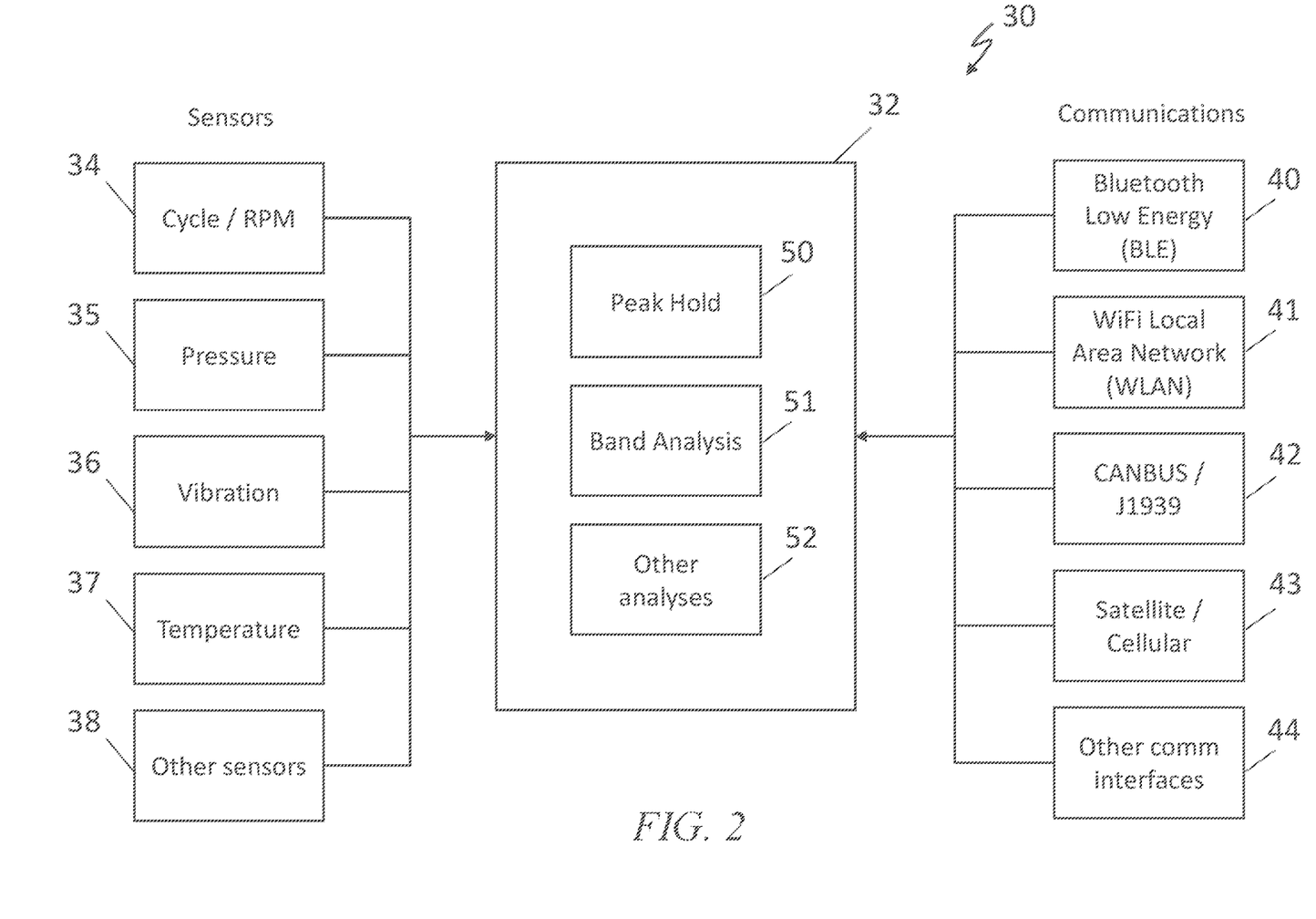
FIG. 2 is a simplified block diagram of a system for hydraulic fracturing pump health and performance monitoring according to the teachings of the present disclosure.

FIG. 2 is a simplified block diagram of a system 30 for hydraulic fracturing (frac) pump health and performance monitoring. The system 30 includes an IoT or fog network co-located with a frac pump at a frac site. The system 30 includes a microcontroller or microprocessor (hereinafter referred to as a microcontroller) 32 that is coupled to and receives operating parameter measurements from a plurality of sensors 34-38 in or on the pump. In addition, the system 30 includes one or more communication interfaces 40-44 configured for transmitting measurement data, analysis data, predicted fault data, and other data to one or more devices to provide a user or another system with pump health or performance information.

The sensors 34-38 are configured to detect conditions of the hydraulic fracturing pump, including, for example, operating conditions of the pump or conditions of the fluid passing through the pump and can be low power custom sensors on the pump that provide real time reporting of operating conditions. The sensors can be mixed mode electronics (e.g., an integrated circuit that has both analog and digital components on a single semiconductor die) and can include one or more cycle and/or RPM sensors 34, one or more pressure sensors 35, one or more vibration sensors 36, one or more temperature sensors 37, and possibly other sensors. For example, in some implementations, the system may include a discharge pressure sensor, a suction pressure sensor, a fluid end vibration sensor, a power end vibration sensor, an rpm sensor, and a cycle sensor. Other combinations of sensors are also possible and can include some or all of the sensors described above. Some implementations may also include a combination of sensors that are different from any of the sensors listed above.

As additional examples, the combination of sensors can include a sensor such as a pressure transducer disposed in a location on the pump that can sense the discharge fluid pressure. The sensor may be alternatively disposed in a discharge fluid passageway in the pump. Another sensor may be configured to sense crankshaft displacement, such as a reed switch, Hall Effect sensor, or inductive proximity sensor. The microcontroller can be configured with software that is able to determine a cycle count number from the cycle signal. A number of other sensor devices may be incorporated in the system to monitor and measure pump operational parameters. Examples include: strain gauge (e.g., mounted on the metal housing of the fluid end to sense and measure the amount of flex in the housing due to pressure fluctuations of the fluid inside the fluid end), pressure sensor, accelerometer, vibration sensor, piezoelectric element, proximity sensor, linear variable displacement transducer (LVDT), load cell, and flow meter. The system may include one or more of these sensors/devices. Pressure could also be obtained by using load cells located in close proximity to the bore but not necessarily in direct contact with the frac fluids.

The sensors may also be configured to measure, obtain, and determine a number of other operating parameters of a frac pump, e.g.: number of operating hours, cycle count, and the duty cycle. The number of operating hours can be the amount of time, in hours, that the pump is operating equal or above a certain predetermined speed threshold, for example 20 RPM. The cycle count can be determined as the number of times that a crankshaft of the pump has gone through a whole cycle. The duty cycle can be measure as the percentage of total time that the pump is in operation measured as in operation within a certain discharge fluid pressure range.

In some implementations, the microprocessor is located at the frac site, on the monitored pump or other equipment and/or on the same trailer as the monitored equipment and is communicatively coupled to the sensors (e.g., by a hardwired or wireless connection, or using an Internet of Things (IoT) architecture) and configured to analyze data received from the sensors to predict faults in the hydraulic fracturing pump, including faults in one or more particular components. Local signal processing allows indicators and patterns to be detected in real-time, rather than storing data locally or sending data to the cloud. Alternatively, raw data can be sent off site to a cloud computer to do analyze the data and detect or predict faults. Alerts can be then sent back to personnel or equipment at the frac site. Such data and alerts can be sent via wired networks, cellular networks, satellite networks, radios, such as long range (LoRa) radios and/or a Low Power, Wide Area (LPWA) networking protocol (e.g., LoRaWAN® network architecture), or other wireless or wired transmission techniques.

In some implementations, the microprocessor is configured to analyze the data received from at least a subset of the plurality of sensors based on a deterministic model, rather than a statistical model, to detect errors or faults. Using deterministic analysis (e.g., known physics models), the conditions that are known beforehand to be precursors to a fault can be assessed in real time to generate a warning of an impending component failure or other fault. For example, the deterministic analysis may be performed by analyzing a truth table of multiple data values received from the sensors. Thus, precursors to emerging faults in the hydraulic fracturing pump can be identified based on a comparison of values of data received from the sensors to one or more predetermined combinations of sensor data values represented in the truth table. As an example, a combination of certain sensor values, some of which exceed or are less than a corresponding threshold, have a predetermined value, fall within a specific range, or are changing above or below a particular rate, can be used to identify an emerging fault. The processing of selected sensor values can include, for example, a peak hold (e.g., holding a maximum or minimum value for a hold period) 50, band analysis (e.g., identifying alignments of patterns of values by conducting band matching) 51, or other analyses 52.

Once an emerging fault is identified, a notification can be sent to other systems or personnel, locally and/or remotely. For example, a local mechanic can be notified by phone or BLE (Bluetooth Low Energy) of the emerging fault. Notifications can also be sent, for example, by a local WiFi network to on-site personnel or to remote corporate personnel, or potentially to the cloud. In some implementations, the system can include multiple communication interfaces, including a Bluetooth Low Energy interface 40, a WiFi local area network communication interface 41, a Controller Area Network (CAN) bus (CANBUS) interface 42, a cellular and/or satellite communication network interface 43, and other communication interfaces 44 configured for transmitting health and performance data, including emerging fault data, to other devices or systems. Some implementations may include fewer than all of these communication interfaces or may include different communication interfaces. In some implementations, CANBUS communications can be sent to other devices on a frac trailer and/or communications can be sent using Industrial IOT (IIOT). The receiving devices can generate and/or display a warning message in response receiving the data relating to a predicted fault.

In general, the system described in this specification can be implemented in hardware and software and can be used to detect faults in components of hydraulic fracturing pumps. Mixed mode electronics can be used to continuously capture pressure and vibration related data and processes this to detect faults in internal components. The system can continuously track health and performance data in the form of histograms and can incorporate damage models indicating the true health and performance of the monitored pump or other device. The system can passively capture existing transducer signals and enables a low-cost solution. The system can incorporate multiple modes of communication including BLE, WIFI, CANBUS, and MODBUS. The device can also have low power consumption, enabling it to be either continuously powered or battery powered for years. Communication protocols can be used to send health and performance indicators to a variety of mobile and other devices.

Figure 3:
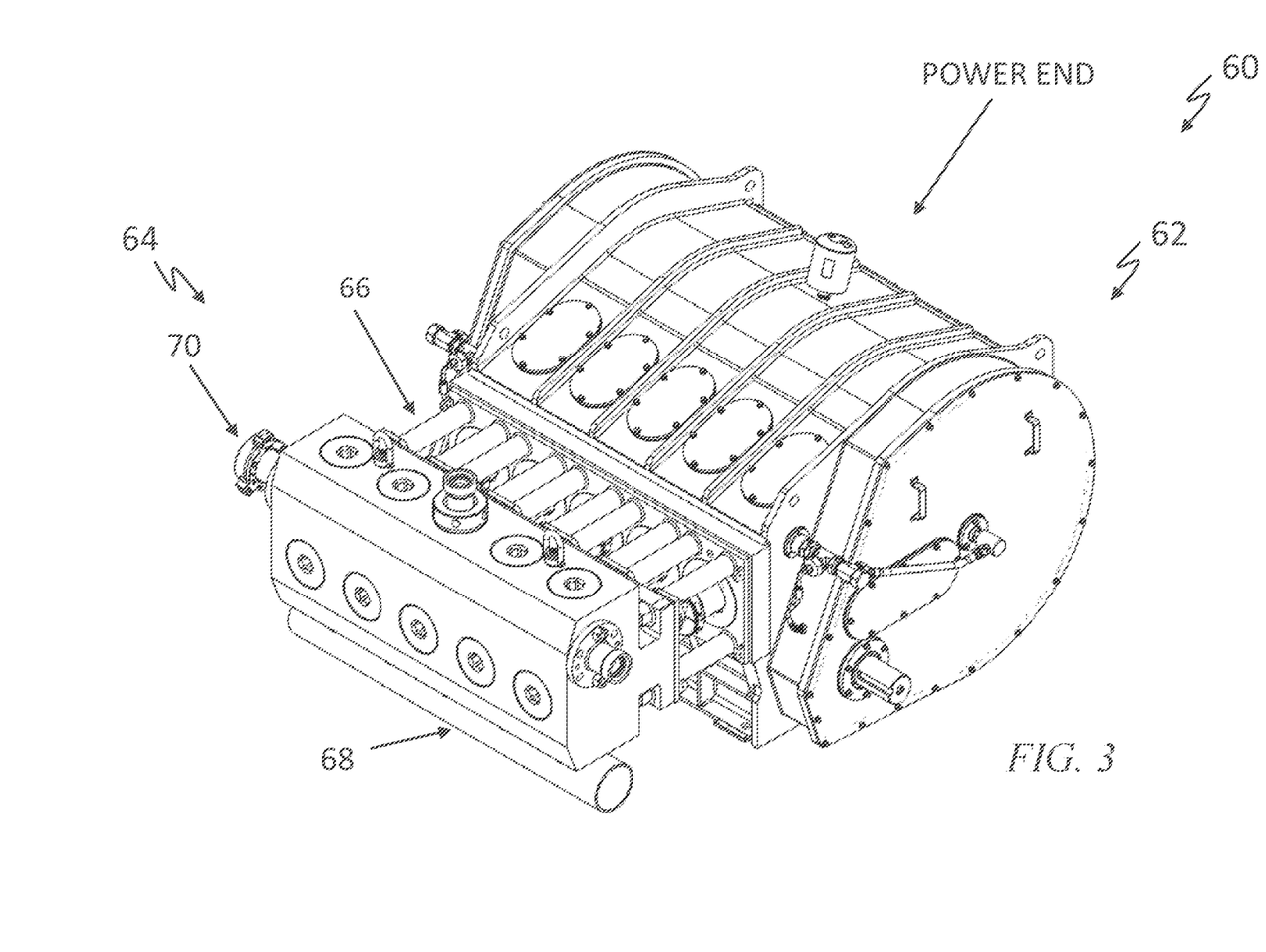
FIG. 3 is a pictorial representation of a positive displacement pump as an example monitoring subject for a system and method for health and performance monitoring according to the teachings of the present disclosure.

FIG. 3 is a pictorial representation of an exemplary positive displacement pump 60 as an exemplary monitoring subject for the system and method described herein. The positive displacement pump 60 has two sections, a power end 62 and a fluid end 64. The fluid end 64 of the pump includes a fluid end block or fluid cylinder, which is connected to the power end housing via a plurality of stay rods 66. In operation, the crankshaft (not explicitly shown) reciprocates a plunger rod assembly between the power end and the fluid end. The crankshaft is powered by an engine or motor (not explicitly shown) that drives a series of plungers (not explicitly shown) to create alternating high and low pressures inside a fluid chamber. The cylinders operate to draw fluid from the suction manifold 68 into the fluid chamber and then discharge the fluid at a high pressure to a discharge manifold 70. The discharged liquid is then injected at high pressure into an encased wellbore. The injected fracturing fluid is also commonly called a slurry, which is a mixture of water, proppants (silica sand or ceramic), and chemical additives. The pump can also be used to inject a cement mixture down the wellbore for cementing operations. The pump may be freestanding on the ground, mounted to a skid, or mounted to a trailer.

Although described in the context of monitoring a frac pump, the system and method may be used to monitor a variety of equipment at a fracturing site. The system and method may also be used to monitor the operations of a slurry blender, fracturing fluid tanks, high-pressure flow iron (pipe or conduit), trailers upon which some equipment are carried, valves, wellhead, charge pump (typically a centrifugal pump), conveyers, and other equipment at the site of a hydraulic fracturing operation or other types of hydrocarbon recovery operations.

Figures 4, 5:
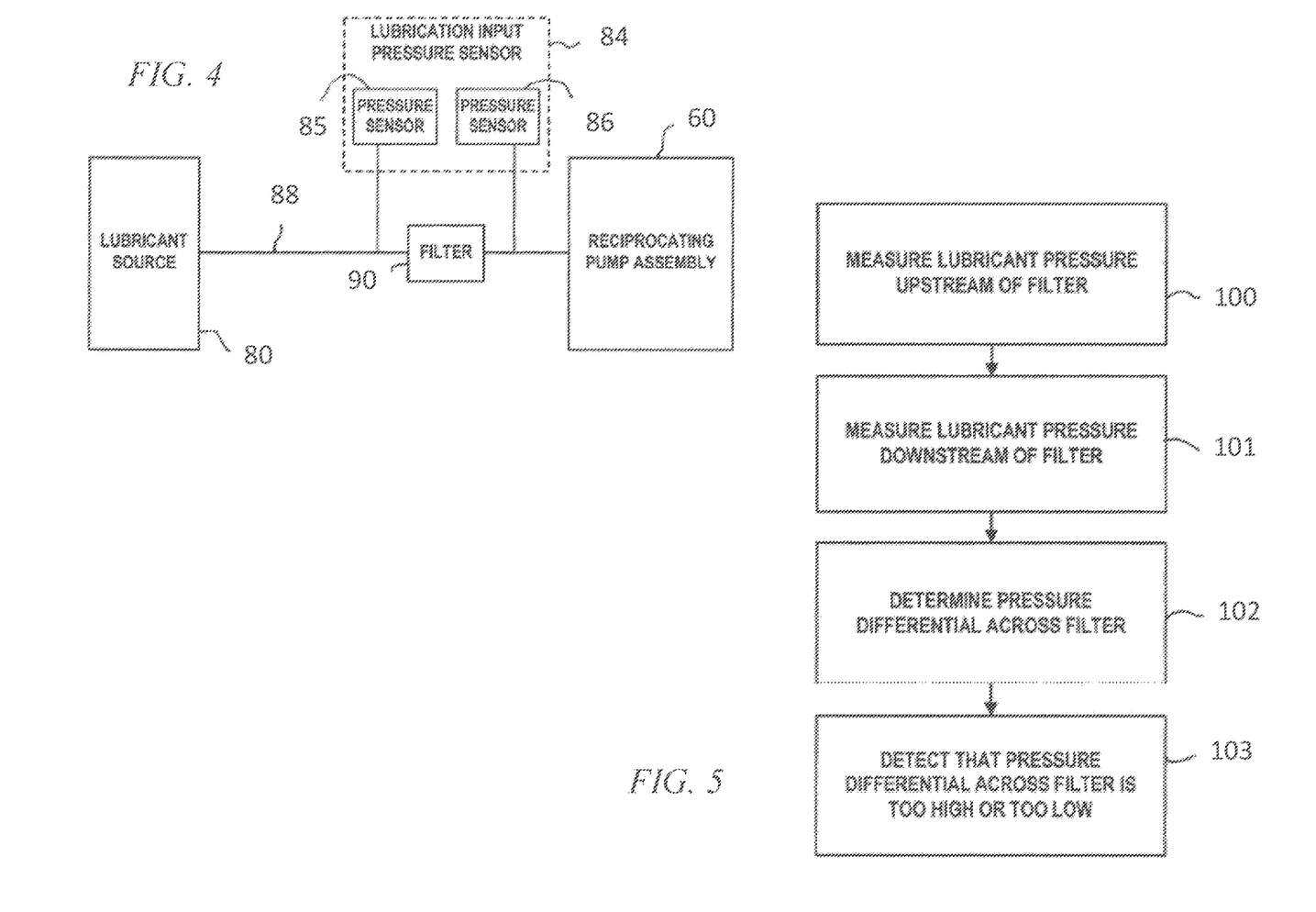
FIG. 4 is a diagrammatic view of a portion of the pump analysis system of the hydraulic fracturing pump system according to the teachings of the present disclosure.
FIG. 5 is a flowchart of a method for analyzing lubrication filter data related to the pump according to the teachings of the present disclosure.
Figure 6:
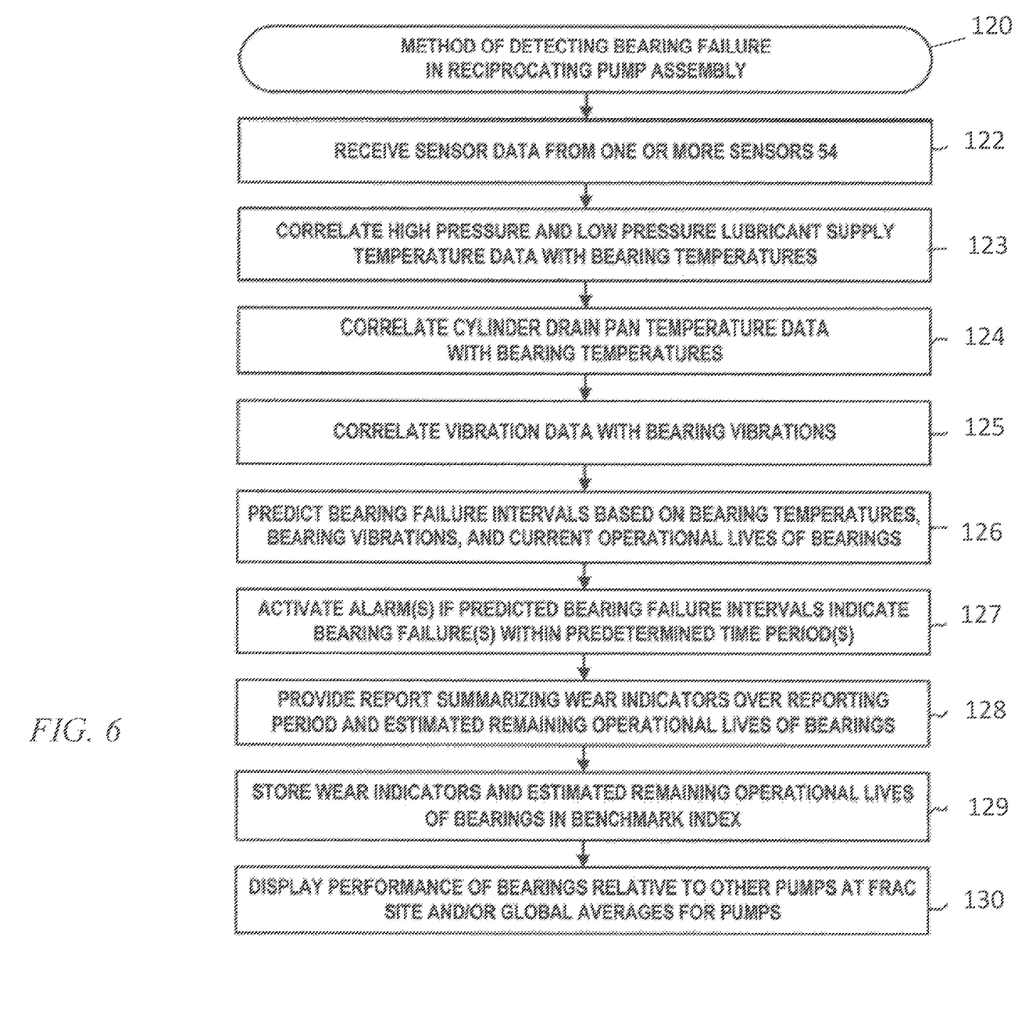
FIG. 6 is a flowchart of a method for analyzing and detecting bearing failure related to the pump according to the teachings of the present disclosure.

In an exemplary embodiment, as illustrated in FIG. 4, a lubricant source 80 is in fluid communication with the reciprocating pump assembly 60 via a lubrication input fluid line 82. In an exemplary embodiment, the lubricant source 80 is an oil tank. A lubrication input pressure sensor 84 includes pressures sensors 85 and 86, each of which is operably coupled to a lubrication input fluid line 88 of a pump, for example. A filter 90 may be operably coupled to the lubrication input fluid line 88 in an in-line configuration. The pressure sensor 85 is operably coupled to the lubrication input fluid line 88 at a position upstream of the filter 90. The pressure sensor 86 is operably coupled to the lubrication input fluid line 88 at a position downstream of the filter 90. In another exemplary embodiment, the pressure sensors 85 and 86 are combined into a single sensor.

In an exemplary embodiment, as illustrated in FIG. 5, the detected event is that the pressure differential across the filter 90 is too high or too low. In steps 100-103, the pressure of the lubricant upstream of the filter 174 is measured, the pressure of the lubricant downstream of the filter 90 is measured, the pressure differential across the filter 90 is determined, and a determination is made that the pressure differential across the filter 90 is either too high or too low based on predetermined settings.

In an exemplary embodiment, all of the steps 100-103 shown in FIG. 5 are performed locally in the IoT network co-located with the pump. The sensors within the network may be smart sensors that are capable of making some of the analysis within the network without requiring transmitting data to a remote central server. Local alarms or alerts may be generated at real-time in response to measurements that are out of safe operating range, for example, and relayed to user devices that are located at the frac site.

In an exemplary embodiment, as illustrated in FIG. 5, a method 120 of detecting bearing failure in the reciprocating pump assembly is shown. Bearing failure in the reciprocating pump assembly may occur when bearings in the power end (roller bearings, shaft pin shell bearings, shell thrust bearings, etc.) become excessively worn due to, for example, prolonged usage, contamination, abusive operation conditions, and/or any combination thereof; in several exemplary embodiments, lead indicators of bearing failure are excessive vibration and high bearing temperatures. As shown in FIG. 5, an embodiment of the method 120 includes: at step 122 receiving sensor data from the one or more sensors; at step 123 correlating high pressure and low pressure lubricant supply temperature data with bearing temperatures; at step 124 correlating cylinder drain pan temperature data with bearing temperatures; at step 125 correlating vibration data with bearing vibrations; at step 126 predicting bearing failure intervals based on the correlated bearing temperatures, correlated bearing vibrations, and current operational lives of the bearings within the reciprocating pump assembly; at step 127 activating alarm(s) if predicted failure intervals indicate bearing failure(s) within predetermined time period(s); at step 128 providing a report summarizing wear indicators over the reporting period and estimated remaining operational lives of bearings; at step 129 storing wear indicators and estimated remaining operational lives of bearings in a benchmark index; and at step 130 displaying performance of bearings within the reciprocating pump assembly relative to other pumps at the frac site (such as the hydraulic fracturing pump system) and/or global averages for pumps. In several exemplary embodiments, the method 120 is executed to detect failure in one or more roller bearings, shaft pin shell bearings, shell thrust bearings, other bearings, etc. within the reciprocating pump assembly; in several exemplary embodiments, one or more of these bearings support the crankshaft, the rotation of which is counted by the crankshaft rotation sensor.

In an exemplary embodiment, at the step 122, sensor data is received from at least one or more of the temperature sensors, and the power end triaxial accelerometer. In an exemplary embodiment, at the step 122, sensor data is received from at least the temperature sensors, the power end triaxial accelerometer, and the fluid end triaxial accelerometer.

In an exemplary embodiment, at the step 123, the high pressure and low pressure lubricant supply temperature data of one or more of the bearings within the reciprocating pump assembly is correlated with bearing temperatures using heat transfer numerical solutions, finite element thermal analyses, heat transfer closed-form solutions, or any combination thereof. In several exemplary embodiments, at the step 123, the high-pressure lubricant supply temperature data is correlated with bearing temperatures using historical experimental and/or operational data (empirical data recorded from past experiments and/or past pump operations). In several exemplary embodiments, at the step 123, the high-pressure lubricant supply temperature data is correlated with bearing temperatures locally in the IoT network.

In an exemplary embodiment, at the step 124, the cylinder drain pan temperature data is correlated with bearing temperatures using heat transfer numerical solutions, finite element thermal analyses, heat transfer closed-form solutions, or any combination thereof. In several exemplary embodiments, at the step 124, the cylinder drain pan temperature data is correlated with bearing temperatures using historical experimental and/or operational data (empirical data recorded from past experiments and/or past pump operations). In several exemplary embodiments, at the step 124, the cylinder drain pan temperature data is correlated with bearing temperatures locally in the IoT network.

In an exemplary embodiment, at the step 125, the vibration data from the reciprocating pump assembly is correlated with bearing vibrations using vibration numerical solutions, finite element dynamic analyses, vibration closed-form solutions, or any combination thereof. In several exemplary embodiments, at the step 125, the vibration data is correlated with bearing vibrations using historical experimental and/or operational data. In several exemplary embodiments, at the step 125, the vibration data is correlated with bearing vibrations locally in the IoT network.

In an exemplary embodiment, at the step 126, bearing failure intervals of one or more of the bearings within the reciprocating pump assembly are predicted based on the bearing temperatures correlated at the steps 123 and 124, the bearing vibrations correlated at the step 125, and current operational lives of the bearings. In an exemplary embodiment, at the step 126, excessive oscillations outside of acceptable tolerances for bearing temperature and bearing vibration are detected, with the excessive oscillations serving as a basis for predicting the bearing failure intervals, thereby determining when one or more bearings within the reciprocating pump assembly will need to be replaced or reconditioned. In several exemplary embodiments, at the step 126, the bearing failure intervals are predicted locally in the IoT network.

Figure 7:
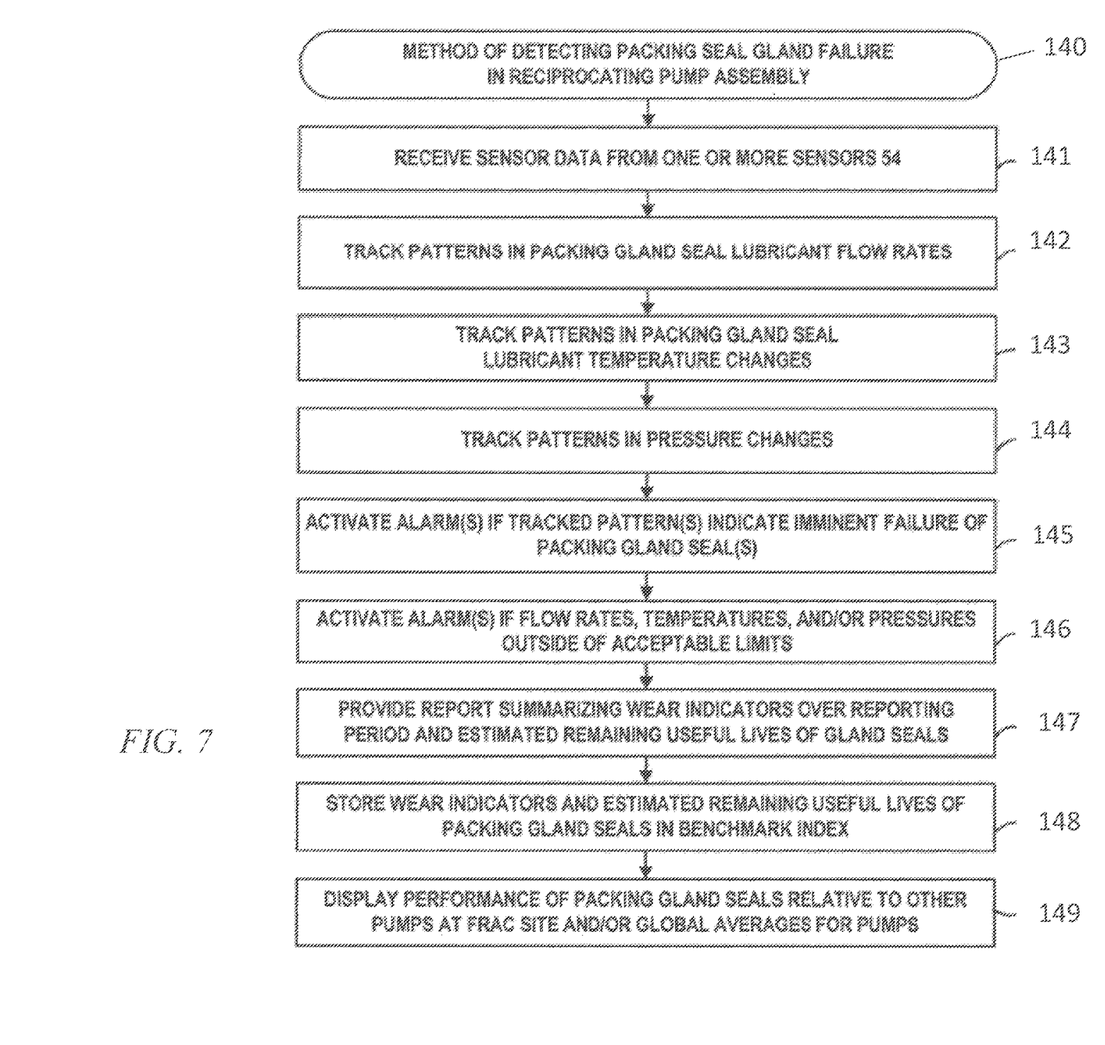
FIG. 7 is a flowchart of a method for analyzing and detecting packing seal gland failure related to the pump according to the teachings of the present disclosure.

As shown in FIG. 7, in an exemplary embodiment, the method 140 includes: at step 141 receiving sensor data from the one or more sensors; at step 142 tracking patterns in packing gland seal lubricant flow rates; at step 143 tracking patterns in packing gland seal lubricant temperature changes; at step 144 tracking patterns in pressure changes; at step 145 activating alarm(s) if tracked pattern(s) indicate imminent failure of packing gland seal(s); at step 146 activating alarm(s) if flow rates, temperatures, and/or pressures are outside of acceptable limits; at step 147 providing a report summarizing wear indicators over the reporting period and estimated remaining useful lives of packing gland seals; at step 148 storing wear indicators and estimated remaining useful lives of packing gland seals in a benchmark index; and at step 149 displaying performance of packing gland seals within the reciprocating pump assembly relative to other pumps at the frac site (such as the hydraulic fracturing pump system 18) and/or global averages for pumps.

Figure 8:
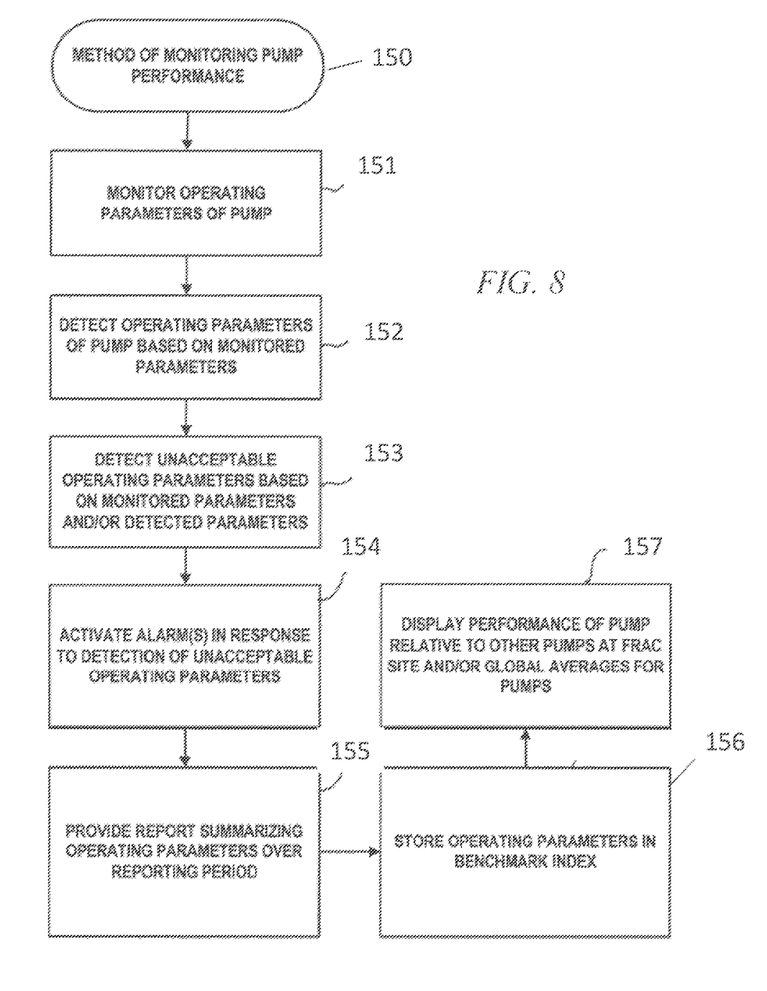
FIG. 8 is a flowchart of a method for analyzing pump performance according to the teachings of the present disclosure.

In an exemplary embodiment, as illustrated in FIG. 8, a method of monitoring pump performance is generally referred to by the reference numeral 150 and includes: at step 151 monitoring operating parameters of the reciprocating pump assembly of the pump system; at step 152 detecting operating parameters of the reciprocating pump assembly; at step 153 detecting unacceptable operating parameters of the reciprocating pump assembly based on the parameters monitored at the step 151 and/or detected at the step 152; at step 154 activating alarm(s) in response to detecting unacceptable operating parameters at the step 153; at step 155 providing a report summarizing operating parameters over the reporting period; at step 156 storing operating parameters in a benchmark index; and at step 157 displaying operating parameters of the reciprocating pump assembly relative to other pumps at the frac site (such as the hydraulic fracturing pump system) and/or global averages for pumps.

Figure 9:
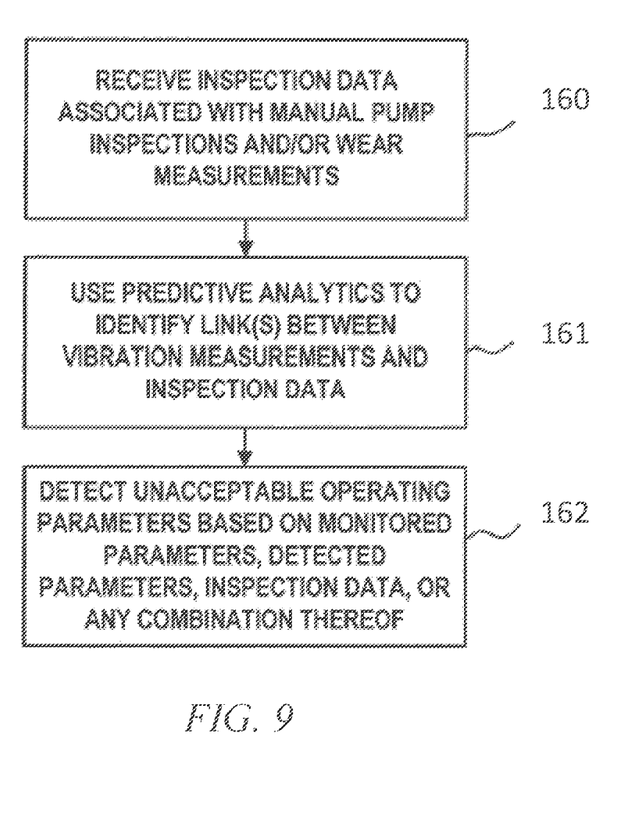
FIG. 9 is a flow chart of a method for analyzing pump performance according to the teachings of the present disclosure.

In another exemplary embodiment, a step of detecting unacceptable operating parameters of the reciprocating pump assembly is shown in FIG. 9. As shown, precursors to cavitation are detected, including suction/discharge line blockages and incorrect valve positions. In an exemplary embodiment, excessive oscillations outside of acceptable tolerances are detected in the monitored/detected vibration data on one or both of the following: the drive side of the power end near the pump gearing (gear box, drive shaft, pinion and bull gear, etc.) and cross heads, etc.; and the fluid end. In an exemplary embodiment, unacceptable variances are detected in or more of the following: pump suction pressure, pump discharge pressure, flow rate, and operating speed; in several exemplary embodiments, such unacceptable variances indicate potential deterioration of pump performance, and/or potential pump failure. In several exemplary embodiments, the detected unacceptable operating parameters (e.g., unacceptable variances in monitored and/or detected pump operating parameters) indicate pump performance deterioration caused by one or more of the following: cavitation; excessive damage on one or more pump parts such as valves, seats, fluid end, bearings, etc.; blockage in suction and/or discharge flow lines; and operating points that have moved away from the pump duty cycle. In an exemplary embodiment, as illustrated in FIG. 9, at step 160 receiving inspection data associated with manual pump inspections and/or wear measurements; at step 161 using predictive analytics to identify link(s) between vibration measurements and the inspection data received at the step 160; and at step 162 detecting unacceptable operating parameters of the reciprocating pump assembly based on the monitored parameters, the inspection data received at the step 160, or any combination thereof. In an exemplary embodiment, at the step 161, the inspection data received at the step 160 is analyzed with respect to the vibration measurements made by the accelerometers, and link(s) between the data and the measurements are identified. In several exemplary embodiments, algorithms are dynamically updated to enable machine learning with respect to detecting unacceptable pump operating parameters; for example, the repeated execution of these steps with different reciprocating pump assemblies reveals that a certain equipment model is susceptible to a particular condition and subsequent executions of the steps are aware of that susceptibility and account for that susceptibility when determining that operating parameters of a particular pump are unacceptable.

Figure 10:
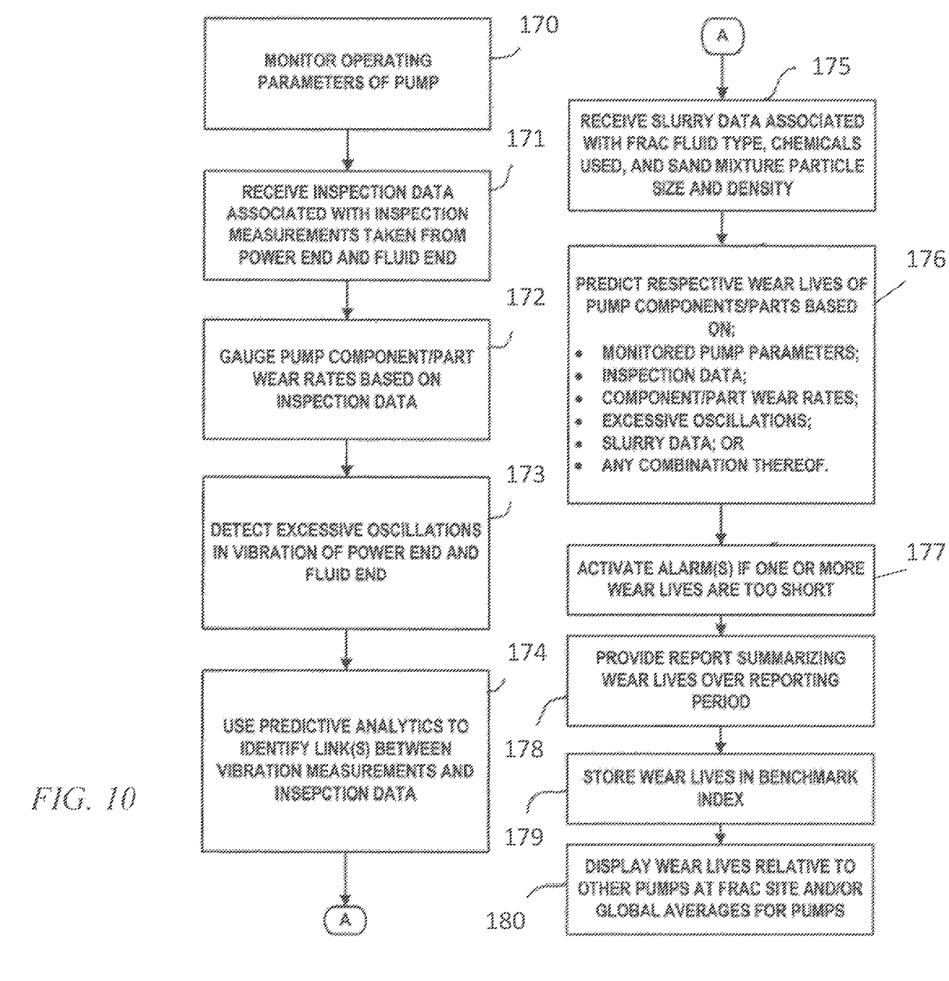
FIG. 10 is a flow chart of a method for analyzing pump operating parameters according to the teachings of the present disclosure.

In an exemplary embodiment, as illustrated in FIG. 10, a method of monitoring wear in the reciprocating pump assembly of the pump system includes: at step 170 monitoring operating parameters of the pump; at step 171 receiving inspection data associated with inspection measurements taken from the power end and/or the fluid end, thereby capturing, for example, pump part damage and/or wear measurements; at step 172 gauging pump component wear rates based on the inspection data received at the step 171; at step 173 detecting excessive oscillations outside of acceptable tolerances in the vibration of the power end and/or the fluid end; at step 174 using predictive analytics to identify link(s) between vibration measurements and the inspection data; at step 175 receiving slurry data associated with the frac fluid type in the slurry, the chemicals used in the slurry, and the sand mixture particle size and density in the slurry; at step 176 predicting respective wear lives, i.e., the respective remaining operational lives, of various parts/components of the reciprocating pump assembly based on the operating parameters monitored at the step 170, the inspection data received at the step 171, the pump component wear rates gauged at the step 172, the excessive oscillations detected at the step 173, the link(s) identified at the step 174, and the slurry data received at the step 175, or any combination thereof; at step 177 activating alarm(s) if one or more wear lives are too short; at step 178 providing reports summarizing wear lives over the reporting period; at step 179 storing wear lives in a benchmark index; and at step 180 displaying respective wear lives of certain components/parts of the reciprocating pump assembly of the pump system relative to other pumps at the frac site (such as the hydraulic fracturing pump system) and/or global averages for pumps.

Figure 11:
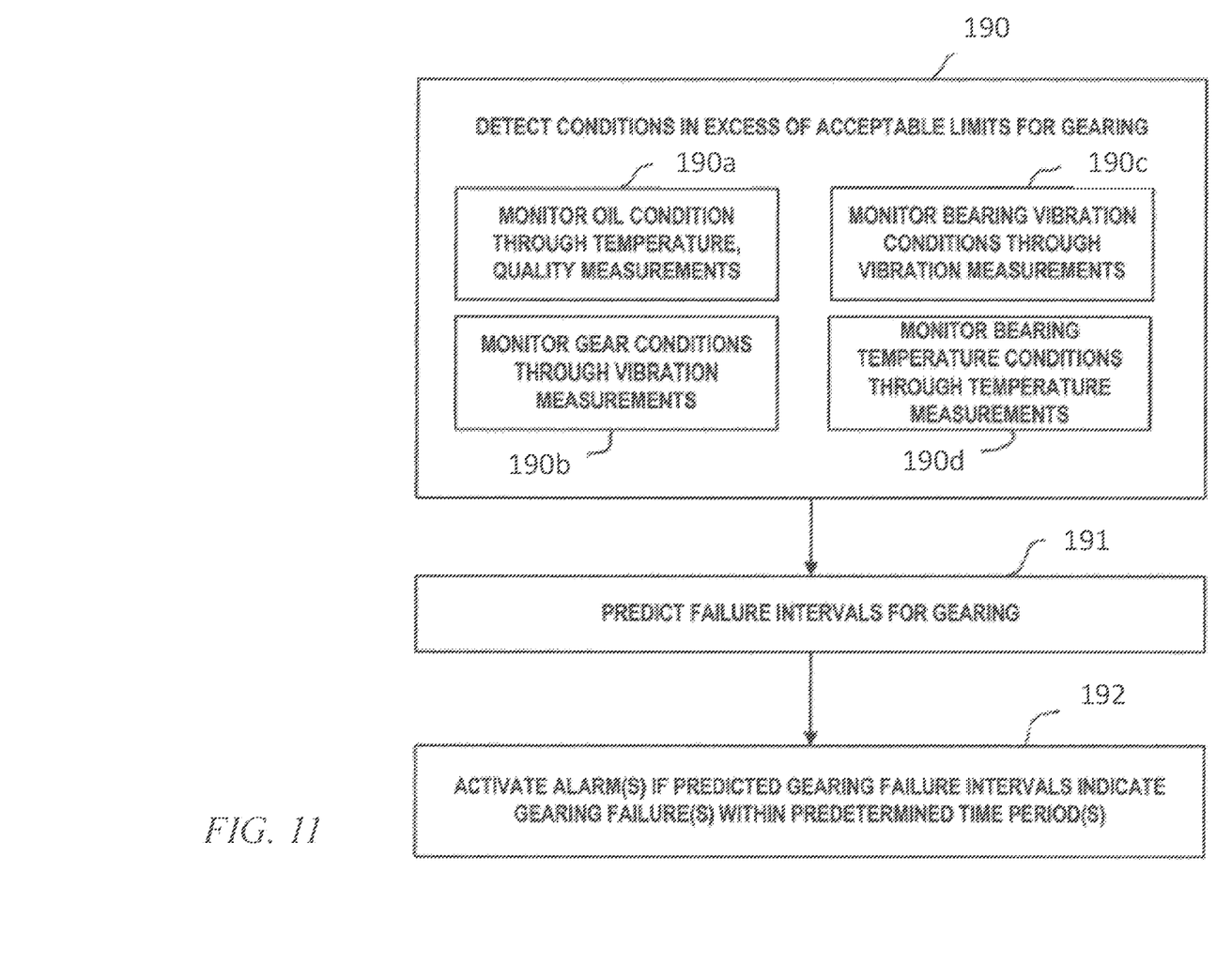
FIG. 11 is a flow chart of a method for monitoring gearing and predicting failure related to the pump according to the teachings of the present disclosure.

In an exemplary embodiment, as illustrated in FIG. 11, a method of monitoring gearing (e.g., gearbox, bull gears, pinion, etc.) in the reciprocating pump assembly of the pump system is shown. The method includes: at step 190 detecting conditions in excess of acceptable limits for the gearing. The step 190 may include monitoring lubricant condition through temperature and/or quality measurements (190*a*), monitor lubricant condition using the measurements taken by the sensors, monitor gear conditions through vibration measurements taken by, for example, the accelerometer, monitor gear vibration conditions through vibration measurements taken by the accelerometers, monitor bearing vibration conditions through vibration measurements taken by, for example, the accelerometer, monitor bearing vibration conditions through vibration measurements taken by the accelerometers, monitor bearing temperatures. At step 191 predicting failure interval(s) for the gearing; and at step 192 activating alarm(s) if gearing failure interval(s) indicate gearing failure(s) within predetermined time periods(s).

According to the disclosure, because data is analyzed locally, alerts, alarms and actionable messages may be generated and transmitted to co-located user devices in real-time. Sensor data and system fault/failure data may be presented to user devices in real-time, stored in database at each frac site and/or at a remote central database, and used to generate a variety of reports locally or remotely (e.g., via a web portal using authorized access).

The features of the present invention which are believed to be novel are set forth below with particularity in the appended claims. However, modifications, variations, and changes to the exemplary embodiments described above will be apparent to those skilled in the art, and the system and method described herein thus encompasses such modifications, variations, and changes and are not limited to the specific embodiments described herein.

What is claimed is:

1. A system for monitoring a hydraulic fracturing pump at a hydraulic fracturing site, comprising:
   a plurality of Internet of Things (IoT) sensors, forming a fog network, coupled to the hydraulic fracturing pump and configured to measure operating parameters of the hydraulic fracturing pump, the plurality of IoT sensors including at least one sensor coupled to a fluid end of the hydraulic fracturing pump and at least one sensor coupled to a power end of the hydraulic fracturing pump;
   a processor an edge computing node, in the fog network, configured to;
      receive measurement data from the plurality of IoT sensors;
      predict a fault in the hydraulic fracturing pump based on the measurement data; and
      generate prediction fault data indicating the fault; and
   a communication interface, in the fog network, configured to transmit, via a local wireless network at the hydraulic fracturing site, the prediction fault data to at least one user device located at the hydraulic fracturing site.

2. The system of claim 1, wherein the measurement data includes at least one of operating conditions of the hydraulic fracturing pump or conditions of fluids passing through the hydraulic fracturing pump.

3. The system of claim 1, wherein the edge computing node is configured to predict the fault in a component of the hydraulic fracturing pump.

4. The system of claim 1, wherein the plurality of IoT sensors include mixed mode electronics.

5. The system of claim 1, wherein the edge computing node, to predict the fault, is configured to analyze the measurement data based on a deterministic model.

6. The system of claim 1, wherein the edge computing node, to predict the fault, is configured to identify precursors to emerging faults in the hydraulic fracturing pump based on a comparison of values of the measurement data to one or more predetermined combinations of sensor data values.

7. The system of claim 1, wherein the communication interface is selected from the group consisting of a WiFi communication interface, a Bluetooth interface, a Bluetooth Low Energy interface, a Controller Area Network bus interface, a wireless local area network interface, a wireless wide area network interface, a cellular communication network interface, and a satellite communication network interface.

8. The system of claim 1, further comprising one or more devices, in the fog network, configured to generate at least one of an alert, an alarm, or a warning message in response to receiving the prediction fault data.

9. The system of claim 1, further comprising a remote central server in communication with the edge computing node and configured to receive the measurement data and the prediction fault data.

10. A method for monitoring a hydraulic fracturing pump, comprising:
receiving, by an edge computing node, measurement data from a plurality of sensors, forming a fog network, coupled to components of the hydraulic fracturing pump and configured to measure operating parameters of the hydraulic fracturing pump;
determining, by the edge computing node, whether the measurement data is indicative of a fault in the hydraulic fracturing pump;
generating, by the edge computing node, prediction fault data indicating the fault; and
transmitting, by the edge computing node via a communication interface using a local wireless network, the prediction fault data to at least one user device.

11. The method of claim 10, wherein receiving the measurement data comprises receiving at least one of operating conditions of the hydraulic fracturing pump or conditions of fluids passing through the hydraulic fracturing pump.

12. The method of claim 10, wherein determining whether the measurement data is indicative of the fault comprises predicting the fault in a component of the hydraulic fracturing pump.

13. The method of claim 10, wherein determining whether the measurement data is indicative of the fault comprises analyzing the measurement data based on a deterministic model.

14. The method of claim 13, wherein analyzing the measurement data comprises identifying precursors to emerging faults in the hydraulic fracturing pump based on a comparison of values of the measurement data to one or more predetermined combinations of sensor data values.

15. The method of claim 10, further comprising generating at least one of an alert, an alarm, or a warning message in response to the prediction fault data.

16. The method of claim 10, further comprising transmitting at least one of the measurement data, the prediction fault data, alarm data, alert data, or warning messages to a remote central server.

17. A system for monitoring a piece of hydraulic fracturing equipment, comprising:
a plurality of sensors, forming a fog network, coupled to the hydraulic fracturing equipment and configured to measure operating parameters of the hydraulic fracturing equipment;
an edge computing node, in the fog network, configured to;
receive measurement data from the plurality of sensors; and
determine a fault in the hydraulic fracturing equipment; and
a communication interface, in the fog network, configured to transmit, via a local wireless network, prediction fault data indicating the fault to at least one user device.

18. The system of claim 17, wherein the measurement data includes at least one of operating conditions of the hydraulic fracturing equipment or conditions of fluids passing through the hydraulic fracturing equipment.

19. The system of claim 17, wherein the edge computing node is configured to determine the fault in a component of the hydraulic fracturing equipment.

20. The system of claim 17, wherein the plurality of sensors include mixed mode electronics.

21. The system of claim 17, wherein the edge computing node, to determine the fault, is configured to analyze the measurement data based on a deterministic model.

22. The system of claim 17, wherein the edge computing node, to determine the fault, is configured to identify precursors to emerging faults in the hydraulic fracturing equipment based on a comparison of values of the measurement data to one or more predetermined combinations of sensor data values.

23. The system of claim 17, wherein the communication interface is selected from the group consisting of a WiFi communication interface, a Bluetooth interface, a Bluetooth Low Energy interface, a Controller Area Network bus interface, a wireless local area network interface, a wireless wide area network interface, a cellular communication network interface, and a satellite communication network interface.

24. The system of claim 17, further comprising one or more devices, in the fog network, configured to generate at least one of an alert, an alarm, or a warning message in response to receiving the prediction fault data.

25. The system of claim 17, further comprising a remote central server in communication with the edge computing node and configured to receive the measurement data and the prediction fault data.

26. The method of claim 10, wherein the plurality of sensors include mixed mode electronics.

* * * * *